United States Patent [19]

Antrim et al.

[11] Patent Number: 4,963,368
[45] Date of Patent: Oct. 16, 1990

[54] OXIDOREDUCTASE ENZYME STABILIZED HIGHLY UNSATURATED FATTY ACIDS AND DERIVATIVES OF SUCH ACIDS

[75] Inventors: Richard L. Antrim; Norman E. Lloyd; James B. Taylor, all of Sparta, N.J.

[73] Assignee: Nabisco Brands, Inc., East Hanover, N.J.

[21] Appl. No.: 182,629

[22] Filed: Apr. 18, 1988

[51] Int. Cl.$^5$ .................. A61K 9/50; A61K 37/50
[52] U.S. Cl. .................. 424/498; 424/190; 424/94.4; 424/94.2
[58] Field of Search .................. 424/94.2, 94.3, 94.4, 424/491, 492, 493, 498, 494; 435/207; 426/10, 61

[56] References Cited

U.S. PATENT DOCUMENTS

| | | | |
|---|---|---|---|
| Re. 23,523 | 7/1952 | Baker | 435/207 |
| 3,956,172 | 5/1976 | Saeki et al. | 424/492 |
| 4,414,334 | 11/1983 | Hitzman | 435/190 |
| 4,526,902 | 7/1985 | Rubin | 514/560 |
| 4,681,896 | 7/1987 | Horrobin | 514/861 |
| 4,867,986 | 9/1989 | Desai et al. | 424/464 |

FOREIGN PATENT DOCUMENTS 0207039  12/1986  European Pat. Off. .............. 426/12
60-49097  3/1985  Japan .

OTHER PUBLICATIONS

Lin, Y., "Inhibition of Lipid Oxidation in Fatty Fish by Glucose Oxidase Preservation", UMI Dissertation Information Service, 1987.

*Primary Examiner*—Jacqueline Stone
*Assistant Examiner*—Jean C. Witz

[57] ABSTRACT

Highly unsaturated fatty acid compounds, and derivatives thereof, are stabilized against oxidation with a water activated oxidoreductase enzyme. The fatty acid containing component is preferably microencapsulated in a wall member which comprises the enzyme.

23 Claims, No Drawings

OXIDOREDUCTASE ENZYME STABILIZED HIGHLY UNSATURATED FATTY ACIDS AND DERIVATIVES OF SUCH ACIDS

BACKGROUND OF THE INVENTION

1. Field of the Invention

The present invention relates to the stabilization of highly unsaturated fatty acids and derivatives thereof. These unsaturated compounds have at least three (3) to six (6) double bonds and would include all the cis forms of 5, 8, 11, 14, 17- eicosapentaenoic acid (EPA), which contains five of such double bonds, and all the cis forms of 4, 7, 10, 13, 16, 19-docosahexaenoic acid (DHA), which contains six of such double bonds, and all the food grade derivatives thereof. The CAS Registry No. of EPA is 10417-94-4 and that of DHA is 6217-54-5. The stabilization is accomplished by the use of certain water activated enzyme containing systems as disclosed hereinafter. The unsaturated compounds are preferably microencapsulated in a wall member containing the enzyme.

2. Description of the Prior Art

EPA and DHA are derived in the form of neutral triglycerides, glycolipids, phospholipids, etc., from marine fats, algae and fungi, and are used in the form of various food grade derivatives thereof, in foods and as a medicament for preventing or ameliorating thrombo-embolic conditions. Because of their highly unsaturated structures, these compounds are very prone to oxidation, and when oxidized may have a highly unpleasant and rancid odor. Upon ingestion, they also cause a phenomenon known, physiologically, as "fish oil belch," which is also an undesirable trait of various of these compounds.

Although various attempts have been made by those in the art to place various of these compounds in a condition or system that would stabilize them against oxidation and render the compounds more organoleptically acceptable during and after ingestion, none have been entirely successful in providing a means to accomplish both ends successfully.

U.S. Pat. Nos. 4,211,865, 4,497,710 and 4,615,839 disclose the preparation of EPA and/or DHA and/or some derivatives thereof.

U.S. Pat. No. 4,526,902, UK Nos. 1,604,554 and 2,033,745 disclose the use of EPA and/or DHA and/or certain derivatives thereof in the treatment or prophylaxis of thrombo-embolic conditions.

U.S. Pat. No. 4,525,306, UK Nos. 1,604,554 and UK 2,033,745 disclose the encapsulation of EPA and/or DHA in capsules of gelatin.

U.S. Pat. No. 4,438,106 discloses the encasing of EPA and DHA and certain derivatives thereof in cyclodextrin.

U.S. Pat. Nos. 4,021,364; 4,225,581; 4,269,821; 4,322,311; 4,324,683; 4,329,332; 4,525,306; UK No. 2,166,651; PCT W086/03676 and PCT WO 86/06252 disclose the encapsulation of various types of biologically active materials or pharmaceuticals in various types of polymeric materials. PCT W086/03676 discloses the use of gelatin as one of such polymeric materials in the coacervation coating process of such publication.

U.S. Pat. Nos. 4,525,306, 4,554,107; 4,623,488; UK Nos. 1,604,554 and 2,033,745 disclose the use of certain antioxidants with EPA and/or DHA, or fish oils containing EPA.

U.S. Pat. Nos. 4,554,107 and 4,623,488 disclose that fish oil containing EPA may be deodorized in a multistep molecular interesterification and distillation process to remove malodorous fractions therefrom.

In a Ph. D. University of Rhode Island dissertation by Yi-Hua Lin, published in 1987, by UNI Dissertation Information Service, 300 N. Zeib Road, Ann Harbor, Michigan 48106, entitled "Inhibition of Lipid Oxidation In Fatty Fish by Glucose Oxidase Preservation", the use of a glucose oxidase/catalase/glucose enzyme system alone, and with an invertase/glucose oxidase/catalase/sucrose system was used to inhibit lipid oxidation in fresh mackeral.

The dissertation also investigated the effects of catalase, glucose oxidase and hemoglobin on lipid oxidation in a model system.

U.S. Pat. No. 3,962,425 discloses that lipophytic enzymes may be used to accelerate the putrefaction of fish.

U.S. Pat. Nos. 4,405,649 and 4,419,370 disclose the use of proteolytic enzymes to treat fish so as to retard curd formation or to liquify the fish.

U.S. Pat. Nos. 3,920,521, 3,997,402 and 4,029,819 disclose the use of superoxide dismutases as antioxidants in foodstuffs containing, inter alia, lipids.

EPA 172,432 discloses the simultaneous use of ascorbic acid oxidase and encapsulated organic acid as a catalyst for use with nitrite picked meats so as to lessen the amounts of nitrites needed to produce red coloration in the meat.

EPA 207,039 discloses the use of certain oxidases and a substrate therefor in combination with catalase and superoxide dismutase to prevent oxidation in beverages and other foods having a pH lower than 5.

OBJECTS OF THE PRESENT INVENTION

An object of the present invention is to provide EPA and DHA and food grade derivatives thereof in a form that will allow these compounds to be stabilized against oxidation while at the same time permit them to be ingested in an organoleptically acceptable fashion.

SUMMARY OF THE INVENTION

It has now been found, according to the present invention, that such object can be readily achieved by microencapsulating the unsaturated compounds in microspheres made of hydrophilic colloids and wherein the walls of the microspheres, preferably, contain an enzyme based stabilizer for the unsaturated compounds.

DESCRIPTION OF THE PREFERRED EMBODIMENT

The Unsaturated Compounds

The unsaturated compounds to be used in the present invention, as noted above, are EPA and DHA and food grade derivatives thereof. These compounds may be used individually, or in various combinations thereof, in the present invention. By "food grade derivatives," it is meant those derivatives of EPA and DHA that are acceptable for use in food and pharmaceutical applications.

The food grade derivatives of EPA and DHA would include mono-, di-, and triglycerides, phospholipids, phosphate lipids, glyco lipids and salts. The salts would include the Na, K and $NH_4$ salts. Other useful derivatives would include amides and esters (i.e., esters of U.S. Pat. No. 4,211,865). A preferred source of the EPA and DHA would be naturally occurring fish oil materials. These fish oils contain about 15 to 30 weight % of the EPA and DHA and derivatives thereof.

The Microspheres

The microspheres which are used to encapsulate the unsaturated compounds have an average particle size of about 20 to 500, and preferably of about 80 to 200, microns. The spheres are made, primarily, of a hydrophilic colloid, as the wall forming material, and are about 0.5 to 10 microns thick. Any food grade hydrophilic colloid may be used for this purpose.

The preferred hydrophilic colloid materials to be used in this regard would include gelatin, alginates, albumin, casein, agar-agar, gum arabic, pectin and starch. The most preferred of such hydrophilic colloids are proteins such as gelatin.

The spheres are so constructed, as described in more detail below, that the walls thereof contain, in weight %, about 1 to 10, and preferably about 1.5 to 3.0, % hydrophilic colloid, and about 97 to 50, and preferably about 88 to 76, % water, and about 0.001 to 0.6, and preferably about 0.002 to 0.006, % enzyme (or about 100 to 60,000, and preferably about 200 to 600 units of enzyme per 100 grams of wall composition), and about 2 to 40, and preferably about 10 to 20, % of substrate for such enzyme.

The enzyme units are one micromole/minute.

The microspheres are formed with the encapsulated unsaturated compounds therein so that the composite materials comprise about 80 to 95 weight % of the encapsulated compounds, or compositions, or oils, containing such compounds and about 5 to 20% weight of encapsulating wall material.

The water content of the wall member is used to provide an activation medium for the enzyme. Such activation amounts of water basically arise from the amounts of water that were used to initially place the encapsulating colloid in a pliable form from which the wall member was initially formed.

The Enzymes and Substrates Therefor

The enzymes which may be used in the present invention are those enzymes that are adapted to scavenge, or enzymatically remove, molecular oxygen which comes in contact with the enzyme at temperatures of about 30° to 110° F. These enzymes are oxidoreductases, that is, enzymes that catalyze oxido-reductions. These enzymes act as electron acceptors and produce $H_2O_2$ or $H_2O$, in the presence of free water and the molecular oxygen. These enzymes, and the substrates that may be used therewith, include the following:

| Enzyme | Substrate |
|---|---|
| Enzymes which react with oxygen as an acceptor and act on a CH—OH group of the donar/substrate.* | |
| malate oxidase | (S)-malate |
| glucose oxidase | $\beta$-D-glucose |
| hexose oxidase | $\beta$-D-glucose |
| cholesterol oxidase | cholesterol |
| aryl alcohol oxidase | aromatic primary alcohol |
| L-gulonolactone oxidase | L-gulono-1,4-lactone |
| galactose oxidase | D-galactose |
| pyranose oxidase | D-glucose |
| L-sorbose oxidase | L-sorbose |
| pyridoxin 4-oxidase | pyridoxin |
| alcohol oxidase | primary alcohol |
| catechol oxidase (dimerizing) | catechol |
| (S)-2-hydroxyacid oxidase | (S)-2-hydroxyacid |
| ecdysone oxidase | ecdysone |
| choline oxidase | choline |
| secondary-alcohol oxidase | secondary alcohol |
| 4-hydroxymandelate oxidase | (S)-2-hydroxy-2-(4-hydroxypenyl) acetate |
| long-chain-alcohol oxidase | long chain alcohol |
| glycerol-3-phosphate oxidase | sn-glycerol-3-phosphate |
| xanthine oxidase | xanthine |
| thiamin oxidase | thiamin |
| L-galactonolactone oxidase | L-galactono-1,4-lactone |
| Enzymes that react with oxygen as an acceptor and act on an aldehyde or keto group of the donor/substrate.* | |
| aldehyde oxidase | aldehyde |
| pyruvate oxidase | pyruvate |
| oxalate oxidase | oxalate |
| glyoxylate oxidase | glyoxylate |
| pyruvate oxidase (CoA-acetylating) | pyruvate |
| indole-3-acetaldehyde oxidase | indole-3-acetaldehyde |
| pyridoxal oxidase | pyridoxal |
| Enzymes that react with oxygen as an acceptor and act on a CH—CH group of the donor/substrate.* | |
| dihydroorotate oxidase | (S)-dihydro-orotate |
| lathosterol oxidase | 5$\alpha$-cholest-7-en-3$\beta$-ol |
| coproporphyrinogen oxidase | coproporphyinogen-III |
| protoporphyrinogen oxidase | protoporphyrinogen-IX |
| bilirubin oxidase | bilirubin |
| Enzymes that react with oxygen as an acceptor and act on a CH—NH$_2$ group of the donor/substrate.* | |

| Enzyme | Substrate |
| --- | --- |
| D-aspartate oxidase | D-aspartate |
| L-amino acid oxidase | L-amino acid |
| D-amino acid oxidase | D-amino acid |
| amine oxidase (flavin containing) | RCHNH$_2$ (where R is preferably a C$_1$ to C$_4$ aliphatic hydrocarbon radical) |
| pyridoxamine phosphate oxidase | pyridoamine 5$^1$-phosphate |
| D-glutamate oxidase | D-glutamate |
| ethanolamine oxidase | ethanol amine |
| putrescine oxidase | putrescine |
| L-glutamate oxidase | L-glutamate |
| cyclohexylamine oxidase | cyclohexylamine |
| protein-lysine 6-oxidase | peptidyl-L-lysyl-peptide |
| L-lysine oxidase | L-lysine |
| D-glutamate (D-aspartate) oxidase | D-glutamate |
| L-aspartate oxidase | L-aspartate |

Enzymes that react with oxygen as an acceptor and act on a CH—NH group of the donor/substrate.*

| Enzyme | Substrate |
| --- | --- |
| sarcosine oxidase | sarcosine |
| N-methylamino-acid oxidase | N-methyl amino acid |
| N$^6$-methyl-lysine oxidase | N$^6$-methyl-L-lysine |
| (S)-6-hydroxynicotine oxidase | (S)-6-hydroxynicotine |
| (R)-6-hydroxynicotine oxidase | (R)-6-hydroxynicotine |

Enzymes that react with oxygen as an acceptor and act on other miscellaneous nitrogenous compounds as the donor/substrate.*

| Enzyme | Substrate |
| --- | --- |
| nitroethane oxidase | nitroethane |
| acetylindoxyl oxidase | N-acetylindoxyl |
| urate oxidase | urate |
| hydroxylamine oxidase | hydroxylamine |

Enzymes that react with oxygen as an acceptor and act on a sulfur containing group of the donor/substrate.*

| Enzyme | Substrate |
| --- | --- |
| sulphite oxidase | sulphite |
| thiol oxidase | R$^1$C(R)SH or R$^1$C(R)S—S(R)R$^1$ wherein R$^1$ is preferably a C$_1$-C$_4$ monovalent hydrocarbon and R is preferably a C$_1$ to C$_4$ divalent hydrocarbon |

Enzymes that react with oxygen as an acceptor and act on a HEME group of the donor/substrate.*

| Enzyme | Substrate |
| --- | --- |
| cytochrome-c oxidase | Ferrocytochrome c |
| Pseudomonas cytochrome oxidase | Ferrocytochrome c$_2$ |

Enzymes that react with oxygen as an acceptor and act on a diphenol or a structurally related donor/substrate.*

| Enzyme | Substrate |
| --- | --- |
| catechol oxidase | catechol |
| laccase | benzenediol |

Enzymes that react with molecular oxygen as an acceptor and act on various types of donor/substrates.*

| Enzyme | Substrate |
| --- | --- |
| catechol 1,2-dioxygenase | catechol |
| catechol 2,3-dioxygenase | catechol |
| protocatechuate 3,4-dioxygenase | 3,4-dihydroxybenzoate |
| gentisate 1,2-dioxygenase | 2,5-dihydroxybenzoate |
| homogentisate 1,2-dioxygenase | homogentisate |
| 3-hydroxyanthranilate 3,4-dioxygenase | 3-hydroxyanthranilate |
| protocatechuate 4,5-dioxygenase | protocatechuate |
| 2,5-dihydroxypyridine 5,6-dioxygenase | 2,5-dihydroxypyridine |
| 7,8-dihydroxykynurenate 8,8a-dioxygenase | 7,8-dihydroxykynurenate |
| tryptophan 2,3-dioxygenase | L-tryptophan |
| lipoxygenase | linoleate |
| ascorbate 2,3-dioxygenase | ascorbate |
| 2,3-dihydroxybenzoate 3,4-dioxygenase | 2,3-dihyroxybenzoate |
| 3,4-dihydroxyphenylacetate 2,3-dioxygenase | 3,4-dihydroxyphenyl acetate |
| 3-carboxyethylcatechol 2,3-dioxygenase | 3-(2,3-dihydroxyphenyl) propanoate |
| indole 2,3-dioxygenase | indole |
| sulfur dioxygenase | sulfur |
| cysteamine dioxygenase | cysteamine |
| cysteine dioxygenase | L-cisteine |
| β-carotene 15,15'-dioxygenase | β-carotene |
| caffeate 3,4-dioxygenase | 3,4-dihydroxy-trans-cinnamate |
| 2,3-dihydroxyindole 2,3-dioxygenase | 2,3-dihydroxyindole |
| quercetine 2,3-dioxygenase | quercetin |
| 3,4-dihydroxy-9,10-secoandrosta- | 3,4-dihydroxy-9,10- |

-continued

| Enzyme | Substrate |
| --- | --- |
| 1,3,5(10)-triene-9,17-dione 4,5-dioxygenase | secoandrosta-1,3,5 (10)-triene-9,17-dione |
| peptide-tryptophan 2,3-dioxygenase | peptidetryptophan |
| 4-hydroxyphenylpyruvate dioxygenase | 4-hydroxyphenyl-pyruvate |
| 2,3-dihydroxybenzoate 2,3-dioxygenase | 2,3-dihydroxybenzoate |
| stizolobate synthase | 3,4-dihydroxy-L-phenylalanine |
| stizolobinate synthase | 3,4-dihydroxy-L-phenylalanine |
| arachidonate 12-lipoxygenase | archidonate |
| 2-nitropropane dioxygenase | 2-nitropropane |
| arachidonate 15-lipoxygenase | arachidonate |
| arachidonate 5-lipoxygenase | arachidonate |
| pyrogallol 1,2-oxygenase | 1,2,3-trihydroxy benzene |
| chloridazon-catechol dioxygenase | 5-amino-4-chloro-2-(2,3-dihydroxy phenyl)-3(2H)-pyridazinone |
| Enzymes that internally react with one atom of oxygen and act on various types of donor/substrates.* | |
| arginine 2-monooxygenase | L-arginine |
| lysine 2-monooxygenase | L-lysine |
| tryptophan 2-monooxygenase | L-tryptophan |
| lactate 2-monooxygenase | L-lactate |
| Renilla-luciferin 2-monooxygenase | Renilla luciferin |
| Cypridina-luiferin 2-monooxygenase | Cyrpidina luciferin |
| Photinus-luciferin 4-monooxygenase | Photinus luciferin |
| Watasemia-luciferin 2-monooxygenase | Watasemia luciferin |

*The listing of enzymes and related substrates which may be used in this regard was extracted from "Enzyme Nomenclature", Recommendations (1984) of the International Union of Pure And Applied Chemistry and the International Union of Biotechnology, Section 1, Oxidoreductases. The related reaction scheme for each of the enzymes is also disclosed in such publication, but is not duplicated here. The disclosures of such publication relative to such reactions is hereby incopo rated herein by reference.

*The listing of enzymes and related substrates which may be used in this regard was extracted from "Enzyme Nomenclature", Recommendations (1984) of the International Union of Pure And Applied Chemistry and the International Union of Biotechnology, Section 1, Oxidoreductases. The related reaction scheme for each of the enzymes is also disclosed in such publication, but is not duplicated here. The disclosures of such publication relative to such reactions is hereby incorporated herein by reference.

The enzymes to be used in the present invention may be obtained from any source thereof.

The most preferred of such enzymes is glucose oxidase, which is usually employed in combination with catalase and in accordance with the following two step reaction scheme.

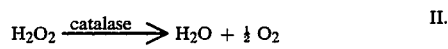

Although molecular oxygen is formed in this process, which process is primarily intended to scavenge oxygen in accordance with the intentions of the present invention, the process does, in fact, produce a net loss of oxygen, relative to the amount of oxygen initially sought to be scavenged.

In selecting an enzyme/substrate system to be used in the present invention, it is also desirable to avoid the use of such systems that may contain metals that have an election transfer capability or other free radical generators that might interfere with the desired antioxidation process. Enzyme based systems that tend to contain metals of this type are, for example, those based on galactose oxidase and bilirubin oxidase. Such metals to be avoided would include Fe, Zn, Cu, and Mo.

The enzyme systems of the present invention contain non-metal based election transfer systems based on the use therein, for example, of flavoproteins.

The enzyme/substrate system can be used in emulsified or non-emulsified form. When emulsified, the enzyme/substrate can be used in an oil-in-water or water-in-oil emulsion.

Microencapsulation Process

The enzyme/substrate systems used in the present invention are used to stabilize the unsaturated compounds by microencapsulating the unsaturated compound in a food-grade hydrocolloid and by incorporating the enzyme/substrate system with the encapsulated unsaturated compound. Alternatively, the enzyme/substrate system can be used only in the wall member used to encapsulate only the unsaturated compound, or the enzyme/substrate system can be incorporated both with the encapsulated unsaturated compound as well as within the encapsulating wall member.

The hydrocolloid materials that may be used in this regard would include gelatin, alginates, albumin, casein, agar-agar, gum arabic, pectin and starch. The preferred of such hydrocolloid materials are the proteins, such as gelatin. The hydrocolloids are also preferably used in crosslinked form. Food-grade crosslinking agents useful for this purpose are known in the art. Food-grade crosslinking agents useful with gelatin, for example, would include glutaraldhyde.

The encapsulation process may employ any of those techniques known in the art for encapsulating enzymes and food grade oils. See for example in this regard "Microencapsulation Processes and Application," edited by Jan E. Vandegaer, Plenum Press, New York, NY, 1974. The contents of this publication are hereby incorporated herein by reference.

The preferred of such processes is coacervation. See pages 21 to 37 of "Microencapsulation Processes and Application," supra, in this regard.

The following Examples are merely illustrative of the scope of the present invention and are not intended as a limitation upon the full scope thereof.

EXAMPLE 1

A batch of about 60 to 70 grams of winterized menhaden fish oil is microencapsulated in gelatin spheres wherein the gelatin is crosslinked with glutaraldehyde. The fish oil contains about 13.6% EPA and about 7.2% DHA in terms of the total fatty acid content of the oil. After the oil is encapsulated in the cross-linked gelatin, the stabilizing enzyme is added to the gelatin walls of the microspheres in a soaking step. The microspheres are about 100-200 microns in average size and contain about 80-85 weight % of oil. The encapsulation process used is a coacervation procedure. The entire process employs the following sequence of steps:

1. 45 mls of 11 percent (w/v) 275 bloom acid precursor gelatin in distilled water containing 50 ppm ethylene diamine tetracetic acid (EDTA) at 55° C. is added to a 250 ml beaker and stirred with a 4-blade impeller (~400 rpm). The EDTA is used as a metal chelator.

2. Temperature is maintained between 52°-56° C. throughout the run.

3. 40 mls of fish oil at 54° C. is added to the gelatin while the stirrer speed is increased to ~1200 rpm. Continue stirring for 2 minutes. Reduce stir speed to ~935 rpm.

4. Add 50 mls of distilled water (54° C.) to stirring emulsion. Increase stir speed to 1100 rpm.

5. Add 10 mls of 54° C. polyphosphate solution.

6. Add 10 percent glacial acetic acid dropwise until pH drops to 4.6 while maintaining temperature at 54° C.

7. Start slowly cooling down the resulting emulsion to 24° C. for approximately 1 hour. (After 30 minutes place in room temperature water bath.) Reduce stirrer speed to ~850 rpm.

8 When coacervate reaches room temperature, place in ice bath and cool to 5° C. Maintain for 30 minutes.

9. Add 2.5 mls of 25 percent glutaraldehyde dropwise into chilled stirring suspension. Allow to stir for 5 minutes and remove from ice bath.

10 Allow to stand overnight for crosslinking.

11. Wash with 4-5 volumes of a 50 ppm aqueous solution of EDTA having a pH of 8.0 and dewater under vacuum.

12. Soak capsules in enzyme and substrate solution overnight, under nitrogen on shaker.

13. Dewater under vacuum to about 70-80% solids content.

EXAMPLES 2-7

Using the procedure of Example 1 microspheres were prepared with fish oil and six different enzyme based systems. The enzymes used in such systems were the following:

A. D-amino acid oxidase (EC 1.4.3.3), from porcine kidney, 7.7 units/mg solid, where one unit will oxidatively deaminate 1.0 micromole of D-alanine to pyruvate per minute at pH 8.3 at 25° C., in the presence of catalase;

B. Catalase (EC 1.11.1.6), from bovine liver, thymol-free, 80% protein, 11,000 units/mg protein, where one unit will decompose 1.0 micromole of $H_2O_2$ per minute at pH 7.0 at 25° C., while the $H_2O_2$ concentration falls from 10.3 to 9.2 micromoles per milliliter of reaction mixture;

C. Choline oxidase (EC 1.1.3.17), from Alcaligenes species, 15 units/mg solid, where one unit will form 1.0 micromole of $H_2O_2$ from choline and $H_2O$ per minute at pH 8.0 at 37° C.;

D. Cytochrome C oxidase (EC 1.9.3.1), from bovine heart, 5 units/mg solid, where one unit will oxidize 1.0 micromole of reduced cytochrome C to 1.0 micromole of oxidized 0 cytochrome C (using 0.5 micromole of oxygen) per minute at pH 7.0 at 37° C.;

E. Cytochrome C reductase (EC 1.6.99.3), from porcine heart, 0.7 units/gr solid, where one unit will reduce 1.0 micromole of oxidized cytochrome C per minute at pH 8.5 at 25° C.;

F. Glucose oxidase (EC 1.1.3.4), from *Aspergillus niger*, 133,000 units/gm solid, where one unit will oxidize 1.0 micromole of beta-D-glucose to D-gluconic acid and $H_2O_2$ per minute at pH 5.1 at 35° C.;

G. L-Lactate 2-monooxygenase (EC 1.13.12.4) from *Mycobacterium smegmatis*, 20.8 units/mg solid, where one unit will oxidatively decarboxylate 1.0 micromole of L-lactate to acetate and $CO_2$ per minute at PH 6.0 at 25° C.;

H. Oxalate oxidase (EC 1.2.3.4) from barley seedlings, 0.7 units/mg solid, where one unit will form 1.0 micromole of $H_2O_2$ from oxalate per minute at pH 3.8 at 37° C.

The enzyme activities and reagent concentrations for the six (6) enzyme based systems studied (based on dilution by the water contained in the microspheres) were the following:

| Example | Enzyme System |
|---|---|
| (2) | D-amino acid oxidase system:<br>pH 7.2,<br>D-amino acid oxidase 5.2 units/ml,<br>catalase 13.6 units/ml,<br>D-alanine 0.68 M,<br>and sodium phosphate 0.34 M |
| (3) | Choline oxidase system:<br>pH 8.0,<br>choline oxidase 67.9 units/ml<br>catalase 136 units/ml,<br>sodium phosphate 0.34 M,<br>and choline chloride 0.68 M |
| (4) | Cytochrome C oxidase system:<br>pH 7.8,<br>cytochrome C oxidase 6.8 units/ml,<br>cytochrome C reductase 4.8 units/ml,<br>cytochrome C 0.55 mM,<br>and NADH 0.096 M |
| (5) | Glucose oxidase system:<br>pH 7.2,<br>glucose oxidase 593 units/ml,<br>catalase 1667 units/ml,<br>glucose 0.68 M,<br>and sodium phosphate 0.34 M |
| (6) | Lactate-2-monooxygenase system:<br>pH 6.0,<br>lactate 2-monooxygenase 13.6 units/ml,<br>and lactate 0.68 M |
| (7) | Oxalate oxidase system:<br>pH 4.0,<br>oxalate oxidase 1.4 units/ml,<br>catalase 13.6 units/ml, |

| Example | Enzyme System |
|---|---|
| | -continued |
| | and oxalic acid 0.085 M |

EXAMPLES 8 to 13

The six samples of encapsulated fish oil/enzyme that were prepared as described in Examples 1 to 7 were then studied for stability purposes to ascertain the extent to which the enzyme prevented oxidation of the EPA and DHA in the fish oils. The stabilization results achieved with the encapsulated enzyme systems of the present invention were matched with stabilization results provided by each of two different control samples of each enzyme based system.

The first control used in this regard was a microencapsulated system prepared as in Example 1 except for the absence of an oxidase enzyme therein. It did contain substrate and catalase (Except for the Examples 4 and 6 systems) components. It is identified hereinafter as the Catalase Control.

The second control is hereinafter identified as the Substrate Control and it was prepared as in Example 1 except for the fact that it did not contain any enzyme or catalase, only substrate.

The enzymic encapsulated fish oil systems were examined at 25° C. in a semiclosed system (exposed periodically to air) over a period of up to over 30 days. The samples were analyzed on an almost daily basis (during the period of Monday to Friday) for peroxide content as a possible indication of rancidity. A system was considered to have become rancid when it had a peroxide value (PV) of $\geq 15$ as determined by the method of Swoboda, P.A.T. and C. H. Lea (Chem. Industry, 1958, August, 1090–1091).

The reactions involved in the use of the Example 2 to 7 enzyme systems to stabilize the EPA/DHA content of the fish oil are shown in Table I below. In some of these reactions, as noted in Table I, (of Examples 1, 3, 5 and 7) $H_2O_2$ is produced, and in the other reactions (of Examples 4 and 6) it is not. In the reaction of Example 4, cytochrome C reductase, which is not an oxidoreductase enzyme, is optionally used to regenerate the substrate, cytochrome C, and thus further prolong the useful oxygen scavenging life of the oxidatoreductase enzyme in accordance with the purposes of the present invention.

TABLE I

ENZYMIC SYSTEMS TESTED FOR STABILIZATION OF FISH OIL OXYGEN SCAVENGING SYSTEMS OF EXAMPLES 2–7 THAT PRODUCT $H_2O_2$ (CATALASE USED TO REMOVE $H_2O_2$)

Example 5. GLUCOSE OXIDASE (EC 1.1.3.4)/CATALASE (EC 1.11.1.6)
  (A) $\beta$-D-GLUCOSE + $O_2$ $H_2O$ → D-GLUCONIC ACID + $H_2O_2$
  (B) $2H_2O_2$ → $O_2$ + $H_2O$ Example 3. CHOLINE OXIDASE (EC 1.1.3.17)/CATALASE (EC 1.11.1.6)
  (A) CHOLINE + $O_2$ → BETAINE ALDEHYDE + $H_2O_2$
  (B) $2H_2O_2$ → $O_2$ + $2H_2O$ Example 7. OXALATE OXIDASE (EC 1.2.3.4)/CATALASE (EC 1.11.1.6)
  (A) OXALATE + $O_2$ → $2CO_2$ + $H_2O_2$
  (B) $2H_2O_2$ → $O_2$ + $2H_2O$ Example 1. D-AMINO ACID OXIDASE (EC 1.4.3.3)/CATALASE (EC 1.11.1.6)
  (A) D-ALANINE + $H_2O$ + $O_2$ → 2-OXOACID + $NH_3$ + $H_2O_2$
  (B) $2H_2O_2$ → $O_2$ + $2H_2O$ Example 4. CYTOCHROME C OXIDASE (EC 1.9.3.1)/CYTOCHROME C REDUCTASE (EC 1.6.99.3)
  (A) REDUCED CYTOCHROME C + $O_2$ → OXIDIZED CYTOCHROME C + $H_2O$
  (B) NADH + OXIDIZED CYTOCHROME C → REDUCED CYTOCHROME C + $NAD^+$ Example 6. L-LACTATE 2-MONOOXYGENASE (EC 1.13.12.4)
  L-LACTATE + $O_2$ → ACETATE + $CO_2$ + $H_2O$ Table II below lists the time, in days, which elapsed before rancidity set in for each of the enzyme systems of Examples 2 to 7, and the corresponding Catalase Control and Substrate Control. This data indicates that the enzyme system of Example 4 was the most active for the purposes of the present invention. Even at the end of 30 days, it was not rancid. It has a peroxide value of only 4.

TABLE II

STABILIZATION OF GELATIN MICROENCAPSULATED FISH OIL AT 25° C. BY VARIOUS OXYGEN-SCAVENGING ENZYMIC SYSTEMS

| | | Time to Rancidity (PV $\geq$ 15) (Days) | | |
|---|---|---|---|---|
| Example | Enzyme System | Enzymic System | Catalase Control | Substrate Control |
| 7 | Oxalate oxidase/catalase | 7 | 7 | 4.5 |
| 3 | Choline oxidase/catalase | 11.8 | 8.5 | 8 |
| 2 | D-amino acid oxidase/catalase | 16.2 | 9.5 | 9.5 |
| 6 | Lactate 2-monooxygenase | 13 | NA | 5.5 |
| 4 | Cytochrome C oxidase/reductase | >30 (4)* | NA | 9.6 |
| 5 | Glucose oxidase/catalase | 20 | NA | 11 |

*Peroxide value at 30 days, rancidity PV $\geq$ 15.
NA = Not Applicable

Table III below indicates the Relative Stability provided by the enzyme systems of the present invention, based on the Table II data. The term Relative Stability means, in this regard, the Time (days) for the enzyme containing system to reach rancidity minus the Time (days) for the Substrate Control to reach rancidity.

TABLE III

Relative Stability Afforded By Various Oxygen-Scavenging Enzymes On Gelatin Microencapsulated Fish Oil At 25° C.

| Example | System | Relative Stability |
|---|---|---|
| 2 | D-amino acid oxidase/catalase | 6.7 |
| 3 | Choline oxidase/catalase | 3.8 |

TABLE III-continued

Relative Stability Afforded By Various Oxygen-Scavenging Enzymes On Gelatin Microencapsulated Fish Oil At 25° C.

| Example | System | Relative Stability |
|---------|--------|--------------------|
| 4 | Cytochrome C oxidase/reductase | >20 |
| 5 | Glucose oxidase/catalase | 9 |
| 6 | L-Lactate 2-monooxygenase | 7.5 |
| 7 | Oxalate oxidase/catalase | 2.5 |

The enzyme stabilized compositions of the present invention may be used, as is, as a source of oxidation stable EPA and DHA for food or drug purposes. Where the EPA and/or DHA are contained in a source material, such as fish oil, which is used in food, drug or cosmetic formulations, the encapsulated and enzyme stabilized source material may be used in such formulations to provide an oxidation resistant source material to such formulations. Thus, for example, fish oils containing EPA and DHA and/or derivatives thereof may be used, in the form of compositions of the present invention, as oils added to or used in food products such as margarine, salad dressings, mayonnaise, and other oil based spreads.

In the context of the present invention, the following terms, as used herein, have the following meanings.
AND=nicotinamide adenine dinucleotide
NADH=reduced nicotinamide adenine dinucleotide

What is claimed is:

1. A stabilized fish oil composition comprising microspheres of a hydrophilic colloid as the wall forming member encapsulating at least one unsaturated compound selected from the group consisting of fatty acids and food grade derivatives thereof having at least three to six unsaturated carbon to carbon double bonds, said wall member containing at least one water activated oxidoreductase enzyme and a substrate donor therefore in amounts effective to stabilize said unsaturated compound.

2. A composition as in claim 1 wherein the hydrocolloid is selected from the group consisting of gelatin, alginates, albumin, casein, agar-agar, gum arabic, pectin and starch.

3. A composition as in claim 2 in which said hydrocolloid is cross-linked.

4. A composition as in claim 3 wherein said unsaturated compound is encapsulated in microspheres having an average particle size of about 20 to 500 microns.

5. A composition as in claim 4 wherein said wall members are about 0.5 to 10 microns thick.

6. A composition as in claim 4 wherein said wall members comprise gelatin as the primary wall forming member thereof.

7. A composition as in claim 6 wherein said microcapsules comprise about 80 to 95 weight % of compositions comprising said unsaturated compound based on the total weight of the microspheres.

8. A composition as in claim 6 in which said unsaturated compound has at least five of said unsaturated bonds.

9. A composition as in claim 6 wherein said unsaturated compound comprises cis-5,8,11,14,17-eicosapentaenoic acid or a derivative thereof.

10. A composition as in claim 6 wherein said unsaturated compound comprises cis-4,7,10,13,16,19-docosahexaenoic acid or a derivative thereof.

11. A composition as in claim 6 in which said enzyme and substrate is selected from the group consisting of D-amino acid oxidase and D-amino acid, choline oxidase and choline, cytochrome C oxidase and cytochrome C, glucose oxide and beta-D-glucose, L-lactate 2-monooxygenase and L-lactate and oxalate oxidase and oxalate.

12. A composition as in claim 6 in which said enzyme comprises D-amino acid oxidase and the substrate is D-amino acid.

13. A composition as in claim 6 in which said enzyme comprises choline oxidase and the substrate is choline.

14. A composition as in claim 6 in which said enzyme comprises cytochrome C oxidase and the substrate is cytochrome C.

15. A composition as in claim 6 in which said enzyme comprises glucose oxidase and the substrate is beta-D-glucose.

16. A composition as in claim 6 in which said enzyme comprises L-lactate 2-monooxygenase and the substrate is L-lactate.

17. A composition as in claim 6 in which said enzyme comprises oxalate oxidase and the substrate is oxalate.

18. A process for stabilizing fish oil having an unsaturated compound of at least five carbon to carbon double bonds therein against oxidation of said double bonds which comprises microencapsulating said unsaturated compound with a hydrophilic colloid as the wall forming material, stabilizing said compound, during the desired period of stabilization, with anti-oxidation and stabilizing effective amounts of at least one water activated oxidoreductase enzyme and a substrate donor therefor placed within said walls of hydrophilic material.

19. A process as in claim 18 in which said enzyme is adapted to produce hydrogen peroxide upon the reaction of oxygen with said substrate.

20. A process as in claim 19 in which said catalase is employed with said enzyme to scavenge said hydrogen peroxide.

21. A process as in claim 20 in which said enzyme is selected from the group consisting of glucose oxidase, choline oxidate, oxalate oxidase and D-amino acid oxidase.

22. A process as in claim 18 in which said oxidoreductase enzyme is used with a substrate that is regenerated in-situ during such process.

23. A process as in claim 22 which employs cytochrome C oxidase and cytochrome C reductase.

* * * * *